(12) United States Patent
Le Doux et al.

(10) Patent No.: US 6,884,613 B2
(45) Date of Patent: Apr. 26, 2005

(54) SELECTIVE PRECIPITATION OF VIRUSES

(75) Inventors: Joseph M. Le Doux, Decatur, GA (US); Martin L. Yarmush, Newton, MA (US); Jeffrey R. Morgan, Sharon, MA (US)

(73) Assignee: The General Hospital Corporation, Boston, MA (US)

( * ) Notice: Subject to any disclaimer, the term of this patent is extended or adjusted under 35 U.S.C. 154(b) by 149 days.

(21) Appl. No.: 09/939,065

(22) Filed: Aug. 24, 2001

(65) Prior Publication Data

US 2002/0081710 A1 Jun. 27, 2002

Related U.S. Application Data

(60) Provisional application No. 60/227,986, filed on Aug. 25, 2000.

(51) Int. Cl.⁷ .................................................. C12N 7/02
(52) U.S. Cl. .................... 435/239; 435/235.1; 210/729; 210/767
(58) Field of Search .............................. 435/239, 235.1; 210/729, 767

(56) References Cited

U.S. PATENT DOCUMENTS 5,447,859 A   9/1995   Prussak

FOREIGN PATENT DOCUMENTS

EP   0 870 839 A1   10/1998

OTHER PUBLICATIONS

Arcasoy et al. (1997) Gene Therapy 4:32–38.

Le Doux et al. (1998) Biotechnology and Bioengineering 58(1):23–34.

Nguyen et al.. (1987) Veterinary Microbiology 14:343–354.

Superti et al. (1993) Comp. Immun. Microbiol. Infect. Dis. 16(1):55–62.

Wallis et al. (1968) Journal of Virology 2(4):267–274.

Primary Examiner—Leon B. Lankford, Jr.
(74) Attorney, Agent, or Firm—Fish & Richardson P.C.

(57) ABSTRACT

The invention provides new methods for purifying and concentrating viruses. The inventors have discovered that high molecular weight proteoglycans present in retroviral stocks are co-concentrated with the retroviruses, and can inhibit retroviral transduction. The new purification and concentration methods feature treatment of virus stock with an anionic polyelectrolyte and a cationic polyelectrolyte, followed by centrifugation. The new methods minimize the amount of proteoglycan co-precipitated with the infectious virus.

27 Claims, 6 Drawing Sheets

SELECTIVE PRECIPITATION OF VIRUSES

CROSS-REFERENCE TO RELATED APPLICATION

This application claims the benefit of U.S. Provisional Application No. 60/227,986, filed Aug. 25, 2000, incorporated herein by reference in its entirety.

STATEMENT AS TO FEDERALLY SPONSORED RESEARCH

This invention was made with Government support under Grant 285285 awarded by the National Institutes of Health and under Grant BE9800617 awarded by the National Science Foundation. The Government may have certain rights in the invention.

FIELD OF THE INVENTION

The invention relates to methods and compositions for purifying and concentrating viruses.

BACKGROUND OF THE INVENTION

Gene therapy involves the transfer of genetic material encoding one or more therapeutic genes and the sequences necessary for their expression to target cells to alter their genetic makeup for some desired therapeutic effect. Gene therapy is being tested in a wide variety of applications, including the treatment of complex genetic disorders such as cancer and infectious diseases such as AIDS, and in tissue engineering. Often, the genetic material is transferred ex vivo to tissue that has been removed from a patient. After gene transfer, the tissue is cultured and expanded in vitro, and then re-implanted into the patient. If the target tissue cannot be removed or cultured in vitro (e.g., brain, heart, lungs), the genetic material is instead injected directly into the patient.

Recombinant retroviruses are the most common gene transfer vector used in human gene therapy clinical trials. However, transduction efficiency is often too low to achieve the desired biological effect in many potential human gene therapy situations. Attempts to improve transduction efficiency by concentrating the retroviruses (e.g., by centrifugation, ultrafiltration, tangential flow, or hollow fiber filtration) have not been very successful. Although retrovirus preparations concentrated by these methods contain higher concentrations of infectious virus, they nonetheless do not transduce significantly more target cells than the unconcentrated stocks. The development of methods that improve transduction efficiency is therefore necessary.

Methods for increasing the sensitivity of assays used to detect disease-causing viruses are also needed. The number of viral particles in a patient's tissue (i.e., viral load) generally correlates well with the rate of progression of associated diseases. To obtain earlier and more accurate diagnoses, and thereby improve patient prognosis, medical personnel need to be able to detect lower viral loads than can be detected with the analytical methods that are currently in widespread use.

SUMMARY OF THE INVENTION

The invention provides new methods for purifying and concentrating viruses. The inventors have discovered that one reason that concentration of retroviruses by the methods described above has not been successful is that high molecular weight proteoglycans present in retroviral stocks are co-concentrated with retroviruses (Le Doux et al., *Biotechnology and Bioengineering*, 58(1):23–34, 1998). The co-concentrated proteoglycans inhibit retroviral transduction. The new purification and concentration methods feature treatment of virus stock with an anionic polyelectrolyte and a cationic polyelectrolyte, followed by centrifugation. The new methods minimize the amount of proteoglycan co-precipitated with the infectious virus.

In general, the invention features a method for purifying viruses from solution (e.g., solutions containing viruses and other components such as proteoglycans). The method includes the steps of (a) combining the solution with an anionic polyelectrolyte; (b) combining the solution with a cationic polyelectrolyte; and (c) centrifuging the solution to obtain a supernatant and a virus-containing pellet. Steps (a) and (b) can be carried out in forward or reverse order, or simultaneously.

The anionic polyelectrolyte can include, for example, a glycosaminoglycan or a polysaccharide, either of which may be sulfated. Examples include chondroitin sulfates, heparin, heparan sulfate, keratan sulfate, carrageenans, fucoidan, poly-L-glutamic acid, poly-L-aspartic acid, other anionic peptides or proteins, poly(glycolic acid), poly(lactic acid), poly(lactic-co-glycolic acid).

The cationic polyelectrolyte can include, for example, a cationic polymer that complexes with the anionic polyelectrolyte. For example, the cationic polyelectrolyte can be (diethylamino)ethyl dextran, a histone, protamine, poly-L-arginine, poly-L-histidine, poly-L-lysine, or another cationic peptide or protein.

The methods can also include the step of separating the pellet from the supernatant, and then resuspending the pellet in a resuspension buffer (e.g., phosphate buffered saline, cell culture medium, or a buffer suitable for injection into a patient (e.g., a pharmaceutically acceptable carrier such as a solution that does not cause allergic or other adverse reaction with the patient upon injection), for example, in a volume of resuspension buffer no greater than one-tenth or one-hundredth the volume of the solution, thereby resulting in at least a ten-fold or one-hundred-fold concentration of the virus, respectively.

The virus to be purified can be, for example, an enveloped virus, such as a lentivirus, Moloney murine leukemia virus (MMLV), herpes simplex virus (HSV), Epstein-Barr virus (EBV), human cytomegalovirus (CMV), an influenza virus, a poxvirus, an alphavirus, or human immunodeficiency virus (HIV) or other retrovirus; or a non-enveloped virus such as an adenovirus, a parvovirus, or a poliovirus.

Another embodiment of the invention features a method for preparing a formulation for administering a nucleic acid molecule to a patient. The method includes the steps of (a) obtaining a solution containing a virus that includes a nucleic acid molecule to be administered to a patient; (b) combining the solution with an anionic polyelectrolyte; (c) combining the solution with a cationic polyelectrolyte; (d) centrifuging the solution to obtain a supernatant and a virus-containing pellet; (e) separating the supernatant from the pellet; and (f) resuspending the pellet in a resuspension buffer suitable for injection into a patient. The method can also include the step of separating the virus from the polyelectrolytes. Steps (a) and (b) can be carried out in forward or reverse order, or simultaneously.

Still another embodiment of the invention features an assay method for detecting the presence of a virus in a sample. The method includes the steps of (a) obtaining a sample to be assayed for the presence of a virus; (b)

combining the sample with an anionic polyelectrolyte; (c) combining the sample with a cationic polyelectrolyte; (d) centrifuging the sample to obtain a supernatant and a pellet (where the pellet includes the virus, if any); and (e) assaying the pellet for the presence of the virus. The method can optionally include the step of resuspending the pellet in a buffer solution, and/or the step of separating the virus from the polyelectrolytes. Steps (a) and (b) can be carried out in forward or reverse order, or simultaneously.

Yet another embodiment of the invention features a kit for use in concentrating or purifying viruses. The kit includes a tube of a suitable size and shape for use in a centrifuge; an anionic polyelectrolyte; and a cationic polyelectrolyte. Optionally, the kit can also include instructions for use. The polyelectrolytes can be supplied in a single tube or in two separate tubes.

The invention provides several advantages. For example, the invention can be scaled up for use in a large-scale manufacturing process. The invention also has many applications in the emerging commercial field of gene therapy that make use of recombinant retroviruses, as well as in any area of research in which cells or tissues are genetically modified using recombinant retroviruses. The methods of the invention can moreover be rapidly performed in a tabletop centrifuge, thus increasing convenience and efficiency and eliminating losses in infectivity due to thermal decay of the viruses.

The new methods advantageously allow rapid concentration and purification of retroviruses without destroying their biological activity and without placing the retroviruses in a solution that is toxic to the target cells to which they will be applied. The invention allows the virus buffer to be rapidly and easily exchanged for a buffer more suitable to the target cells. This can be important where the cell culture medium used to produce virus particles (e.g., DMEM with 10% bovine calf serum) is not suitable for cell types that are potential targets for gene therapy.

The new methods can be used to concentrate viruses to any desired level. The ability to concentrate viruses would substantially improve the effectiveness of many gene therapies, such as those that rely on lentivirus vectors. Lentivirus vectors are of significant interest for use in gene therapy because they can permanently and stably transfer genes into cells and tissues by direct injection in vivo. Lentivirus vectors often fail to achieve the desired therapeutic effect, however, because they have relatively low gene transfer efficiencies and are produced at low titers. Concentrated forms are needed for injection to achieve the desired biological effect. This invention can be used to manufacture stocks of lentivirus vectors that have a high enough concentration to achieve the desired therapeutic effect.

The new methods not only increase transduction efficiency by increasing the concentration of the viruses, they unexpectedly increase transduction by an additional factor of two to three or more beyond the concentration factor, possibly by increasing the encounter frequency of the viruses with the cells.

This invention will also significantly improve the sensitivity of assays designed to detect pathological viruses in large volumes of fluid such as blood or plasma by precipitating the viruses into a small pellet and to a concentration high enough to be detected by current assays. For example, blood or plasma samples can be treated with charged polymers as described above, and the resulting precipitate pelleted and assayed for the presence of pathological viruses. Because the concentration of the pathological viruses would be substantially increased in the pellet, the overall sensitivity of the screening process would be greatly increased, and, as a result, the safety of the tested blood supply improved.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
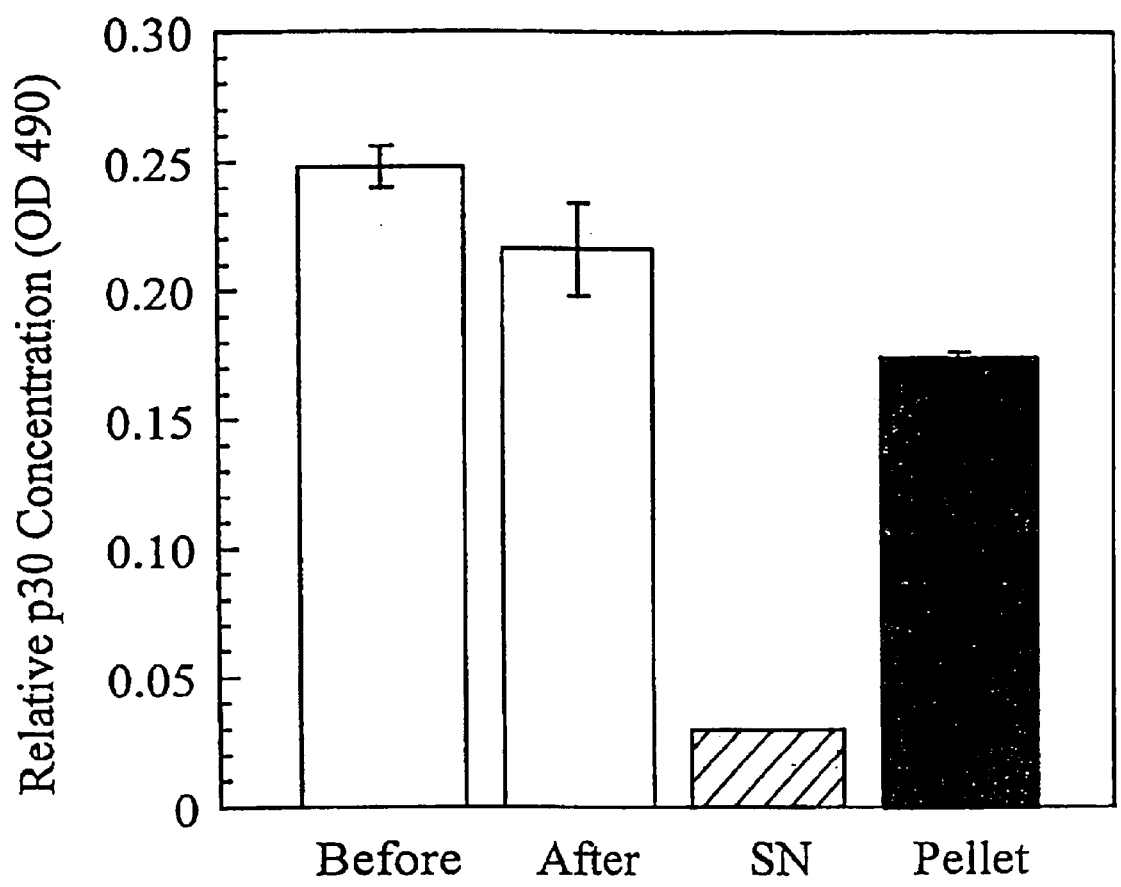
FIG. 1 is a plot of relative virus concentration, indicated by the concentration of capsid protein p30, in a retrovirus solution before mixing with POLYBRENE® and chondroitin sulfate C ("Before"), in the retrovirus solution after mixing with POLYBRENE® and chondroitin sulfate C ("After"), in the supernatant resulting from centrifuging the retrovirus solution ("SN"), and in a solution resulting from resuspending to original volume in phosphate-buffered saline (PBS) the pellet resulting from centrifuging the retrovirus solution. The y-axis represents optical density at 490 nm ($OD_{490}$).

This invention describes a simple and facile method to rapidly and selectively concentrate retroviruses.

The New Methods

In a typical method of the invention, virus stocks are combined with 1 μg/ml to 100 μg/ml of anionic polyelectrolyte (e.g., chondroitin sulfate C; "CSC"), optionally incubated (e.g., for 10 minutes or longer) at 4° C. to 37° C., and then combined with 1 μg/ml to 100 μg/ml of a cationic polyelectrolyte (e.g., POLYBRENE®-brand hexadimethrine bromide), and optionally incubated (e.g., for 0 to 10 minutes, or longer) at 4° C. to 37° C. Alternatively, the cationic polyelectrolyte can be added before, or at the same time as, the anionic polyelectrolyte. Subsequently, a visible pellet is typically formed by low speed centrifugation (e.g., 10,000 rpm for 5 minutes) in a tabletop centrifuge.

The cell culture supernatant that contains the unpelleted material can be removed and the pellet resuspended in a buffer optimized for the culture and transduction of the target cells. The final concentration of the viruses, and the number of therapeutic gene copies that are ultimately delivered to the target cells, are controlled by the volume of buffer used to resuspend the pellet. The pellet can be, for example, resuspended in a volume that is 10- to 100-fold less than the initial volume of the virus stock, so that the final concentration of the viruses is 10- to 100-fold greater than the concentration of the viruses in the original, unpelleted, virus stock.

To transduce the target cells, the cells can be incubated (e.g., at 37° C. for several hours) with the concentrated virus solution (which also contains the polyelectrolytes). Significantly, the efficiency with which the cells transduced in these experiments is 2- to 3-fold higher than expected based on the increased concentration of the viruses alone, as described in Example 1. In other words, if the virus solution is concentrated 10-fold by this technique, the efficiency with which the cells are transduced is 20- to 30-fold higher than the original, unpelleted, virus stock. This unexpected increase in transduction efficiency is probably due to a higher frequency of encounters between the target cells and the viruses due to sedimentation of viruses complexed with polyelectrolytes. That is, the rate at which the virus complexes precipitate onto the cells may occur at a higher rate than would occur between viruses and cells in the absence of polyelectrolytes.

Viruses that can be concentrated by the new methods include retroviruses (e.g., enveloped retroviruses) such as human immunodeficiency virus (HIV), lentiviruses, and Moloney murine leukemia virus (MMLV). The method can also be used to concentrate other enveloped viruses, including herpes simplex virus (HSV), Epstein-Barr virus (EBV), human cytomegalovirus (CMV), influenza viruses, poxviruses, and alphaviruses; or non-enveloped viruses such as adenoviruses, parvoviruses, or polioviruses. Lentivirus vectors are of special interest, because they are able to transfer genes to cells that are not dividing. This ability can provide a major advantage for in vivo gene therapy. The new methods can be used to provide lentiviruses at high enough concentrations to achieve the desired biological effect.

Use of the New Methods in Gene Therapy Applications

Retroviruses can be raised in packaging cell lines, and then harvested. The new methods should be useful with any packaging cell line, including, for example, ψCRIP, FLYA13, and PHOENIX® amphotropic packaging cell lines. Retroviruses can be harvested as follows: Packaging cell lines are grown to confluence. The cell culture medium is removed and replaced with fresh medium and the cells are incubated at 37° C. After a sufficient time (e.g., about 12, 18, 24, or 30 hours), the cell culture medium is removed, filtered (0.45 μm), and frozen for later use as a virus stock. The virus stocks can be mixed with polyelectrolyte solutions according to the methods of the invention (e.g., to increase transduction efficiencies and/or to rapidly concentrate and purify the virus particles from the cell culture medium in which they were grown). After the viruses are precipitated with the polymers and centrifuged to form a pellet, they can be resuspended in any suitable buffer including phosphate buffered saline (PBS), tris-buffered saline, or basal cell culture medium (e.g., Dulbecco's modified Eagle medium, "DMEM"). Resuspended virus particles can be injected into a tissue to be treated, administered orally, nasally, rectally, intravenously, intramuscularly, using a gene gun or other intradermal methods, or by other routes used for drug delivery. A major advantage of this method is that less than 3 percent of non-viral proteins are precipitated with the virus particles, affording a dramatic reduction in, or elimination of, natural inhibitors of retrovirus transduction such as proteoglycans or TGF-β.

Use of the New Methods in Analytical Applications

Current methods for detecting viruses typically assay blood plasma for the presence of markers for a particular virus. In the case of human immunodeficiency virus, for example, these markers include viral RNA and HIV p24 antigen (a virus capsid protein). Viral RNA has traditionally been the marker of choice, in part because RNA assays can make use of the polymerase chain reaction (PCR) to amplify the analyte and are, therefore, generally more sensitive than the enzyme-linked immunosorbent assays (ELISAs) use to detect the antigens such as HIV p24. Although RNA assays tend to be more sensitive, however, they are also more expensive and are not as easy to perform as ELISAs. Cost and sensitivity issues aside, both types of assays have proved to be valuable predictors for certain aspects of the progression of diseases such as AIDS. RNA assays, for example, appear to be better predictors of the clinical progression of the disease, whereas p24 antigen assays appear to be better predictors of the patient's chance of survival.

The new methods can be used to concentrate viruses present in tissue samples before the samples are analyzed, effectively increasing the sensitivity of the analytical methods. Advantageously, the polymers used for virus precipitation in the new methods do not block the ability of standard protocol assays such as ELISAs to detect retrovirus proteins, and should not interfere with PCR reagents.

Polyelectrolytes

In general, any pair or system of charged polymers that can bind to the viruses or otherwise interact with viruses so as to cause them to aggregate or otherwise precipitate rapidly under low speed centrifugation can be used to concentrate viruses.

Preferably, the charged polymers are not toxic to the cells and do not inactivate the viruses. If the charged polymers are cytotoxic, they must be able to be separated from the viruses prior to their application to the target cells. For example, the virus can be dissociated from the polymers using a high-salt buffer that reduces the electrostatic attraction between the virus and polymers. Alternatively, the virus can be dissociated from the polymers by enzymatically degrading one or both of the polymers. For example, CSC can be degraded into individual disaccharides by treating the solution with chondroitinase ABC. Once the polymers have been degraded or dissociated from the virus, the virus can be isolated (e.g., using a gel filtration spin column).

Chondroitin sulfate C and POLYBRENE® together form an examplary pair of polyelectrolytes that can form complexes that can be used to concentrate viruses. However, any pair of polyelectrolytes that includes an anionic polymer (e.g., sulfated glycosaminoglycans or polysaccharides such as chondroitin sulfate A, B, D, or E, heparin, heparan sulfate, keratan sulfate, iota carrageenan, kappa carrageenan, and fucoidan; anionic peptides and proteins such as poly-L-glutamic acid and poly-L-aspartic acid; or biodegradable polymers such as poly(lactic acid), poly(glutamic acid), and poly(lactic-co-glycolic acid)) and a cationic polymer that can complex with the anionic polymer (e.g., POLYBRENE®, (diethylamino)ethyl dextran (DEAE dextran), histones, protamine, or cationic peptides and proteins such as poly-L-lysine, poly-L-arginine, and poly-L-histidine) can be used instead of this exemplary pair. For example, polymer pairs iota carrageenan and DEAE dextran; heparan sulfate and protamine; and L-glutamate and L-lysine can be used.

Virus Concentration Kits

Optionally, the new methods can be carried out using a reagent kit. The kit can include suitable reagents and optionally vessels for carrying out the new methods. Such a kit can be produced and sold in various sizes. For example, a kit for concentrating small volumes of virus-containing medium (e.g., less than about 25 ml) can include a plastic or glass tube, which can contain a solution of a suitable anionic polymer or into which such a polymer can be added from another supplied vessel. The tube can be, for example, a standard centrifuge tube or a similarly sized and shaped tube. After introducing the virus-containing medium into the tube, the tube can be sealed (e.g., using a supplied screw cap), shaken to ensure thorough mixing, and incubated for a suitable time. After incubating, the tube can be opened and a solution containing a suitable cationic polymer can be added (e.g., using a pipettor) to the tube. The tube can then be re-sealed, shaken, and incubated again. Alternatively, the contents of the tube can be decanted after the first incubation step into a second tube that already contains a suitable cationic polymer. The second tube can likewise be sealed, shaken, and incubated. In either case, the tube can be loaded into a centrifuge (or its contents can be decanted into a centrifuge tube and loaded into a centrifuge) after the second incubation step, and spun at a suitable speed. The supernatant resulting from the centrifugation step can then be decanted, being careful not to disrupt the pellet. The pellet might then be washed using an optionally supplied wash solution, and possibly resuspended in a supplied resuspension buffer.

The kits can optionally include enzymes or small spin columns to eliminate or separate, respectively, the viruses from the polymers. The kits can also include a dye, or the polymers can be conjugated to a dye, to make the precipitated virus easy to see with the naked eye, thereby facilitating the resuspension of small volumes of virus. The kit can also include a resuspension buffer optimized for transducing particular cell types or for injection in vivo.

Numerous other embodiments of suitable kits are also contemplated, including kits for use with both tabletop and larger centrifuges.

EXAMPLES

The invention is further described in the following examples, which do not limit the scope of the invention described in the claims.

Example 1

Concentration of MMLV

Stocks of Moloney murine leukemia virus (MMLV) were brought to 80 µg/ml of chondroitin sulfate C, incubated for 10 minutes at 37° C., and then brought to 80 µg/ml of POLYBRENE®, and incubated for an additional 10 minutes at 37° C. The retroviruses, when mixed with POLYBRENE® and chondroitin sulfate C (CSC), were visibly pelleted by low speed centrifugation (i.e., 10,000 rpm for 5 minutes) in a tabletop centrifuge. The visible pellet was resuspended to its original volume with phospate buffered saline (PBS). As shown in FIG. 1, the solution resulting from resuspension of the pellet was then tested for the presence of a virus capsid protein (p30) by ELISA (black bar/"Pellet"). The concentration of p30 in the supernatant was determined after centrifugation (cross hatched bar/"SN"), as was the concentration of p30 in non-centrifuged virus stocks before (white bar/"Before"), and after (speckled bar/"After") POLYBRENE® and CSC were added.

Figure 2:
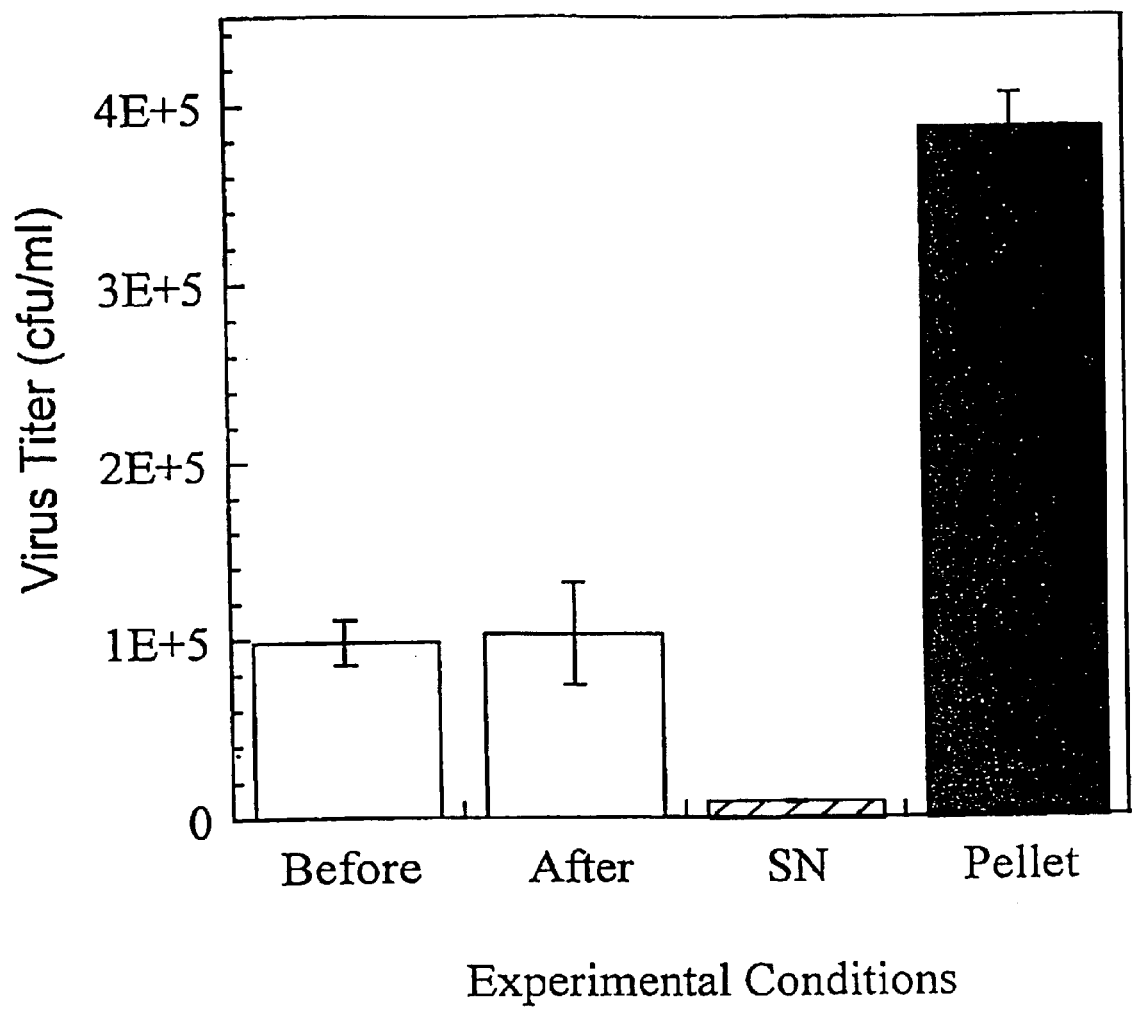
FIG. 2 is a plot of the biological activity of viruses taken from the four samples described in FIG. 1. The y-axis represents virus titer (colony-forming units per milliliter (cfu/ml)).

The solution resulting from the resuspension of the pellet in PBS was tested for its biological activity, using a virus titer assay. The pelleted retroviruses were found to have retained most of their biological activity, as illustrated by the black bar ("Pellet") in FIG. 2. The biological activity in the supernatant (cross hatched bar/"SN") was also determined, as was the biological activity in non-centrifuged virus stocks before (white bar/"Before") and after (speckled bar/"After") POLYBRENE® and CSC were added.

Figure 3:
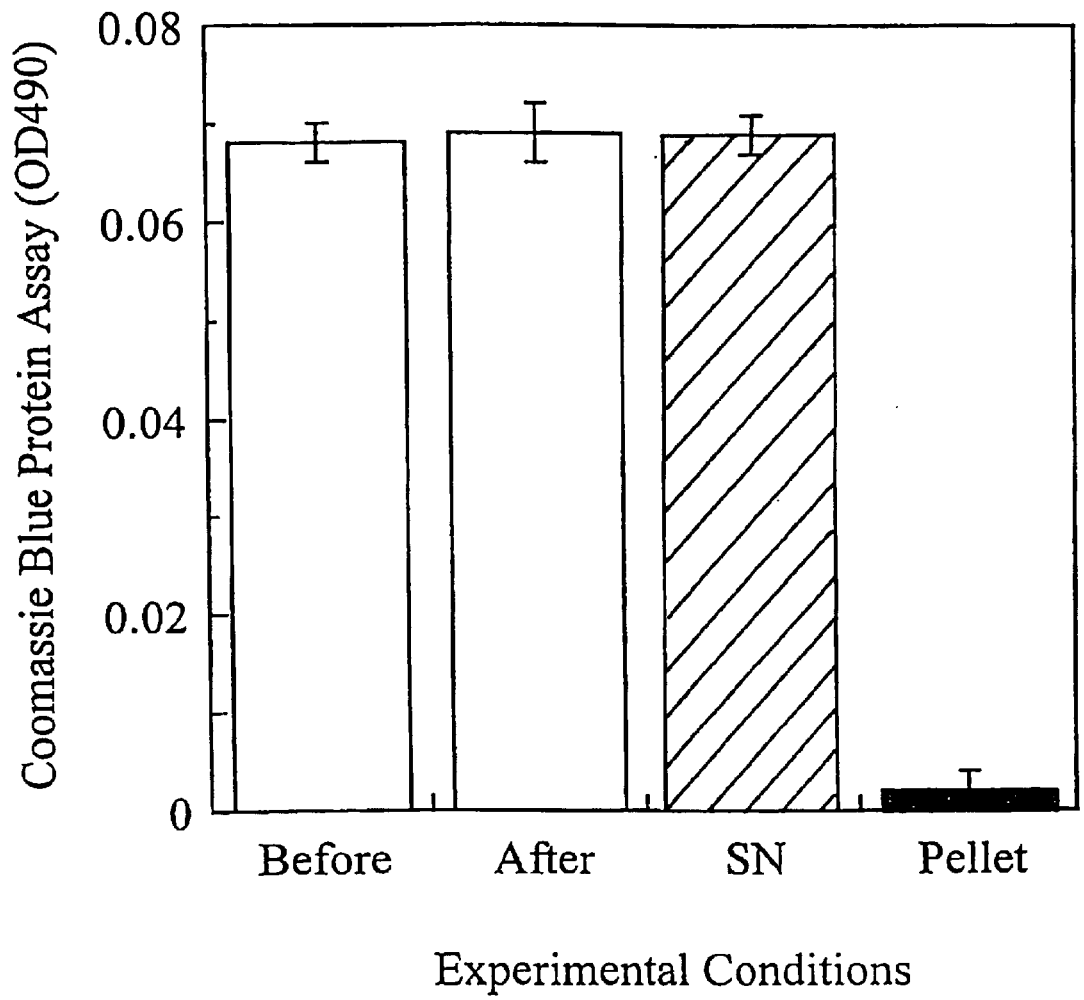
FIG. 3 is a plot of relative concentration of serum proteins in the four samples described in FIG. 1, as indicated using a Coomassie Blue Protein Assay. The y-axis represents OD490.

The solution resulting from the resuspension of the pellet in PBS was tested for total protein concentration. The virus pellets were found to contain very few serum proteins, as illustrated by the black bar ("Pellet") in FIG. 3. The total protein concentration in the supernatant (cross hatched bar/"SN") was also determined, as was the total protein concentration in non-centrifuged virus stocks before (white bar/"Before") and after (speckled bar/"After") POLYBRENE® and CSC were added.

Figure 4:
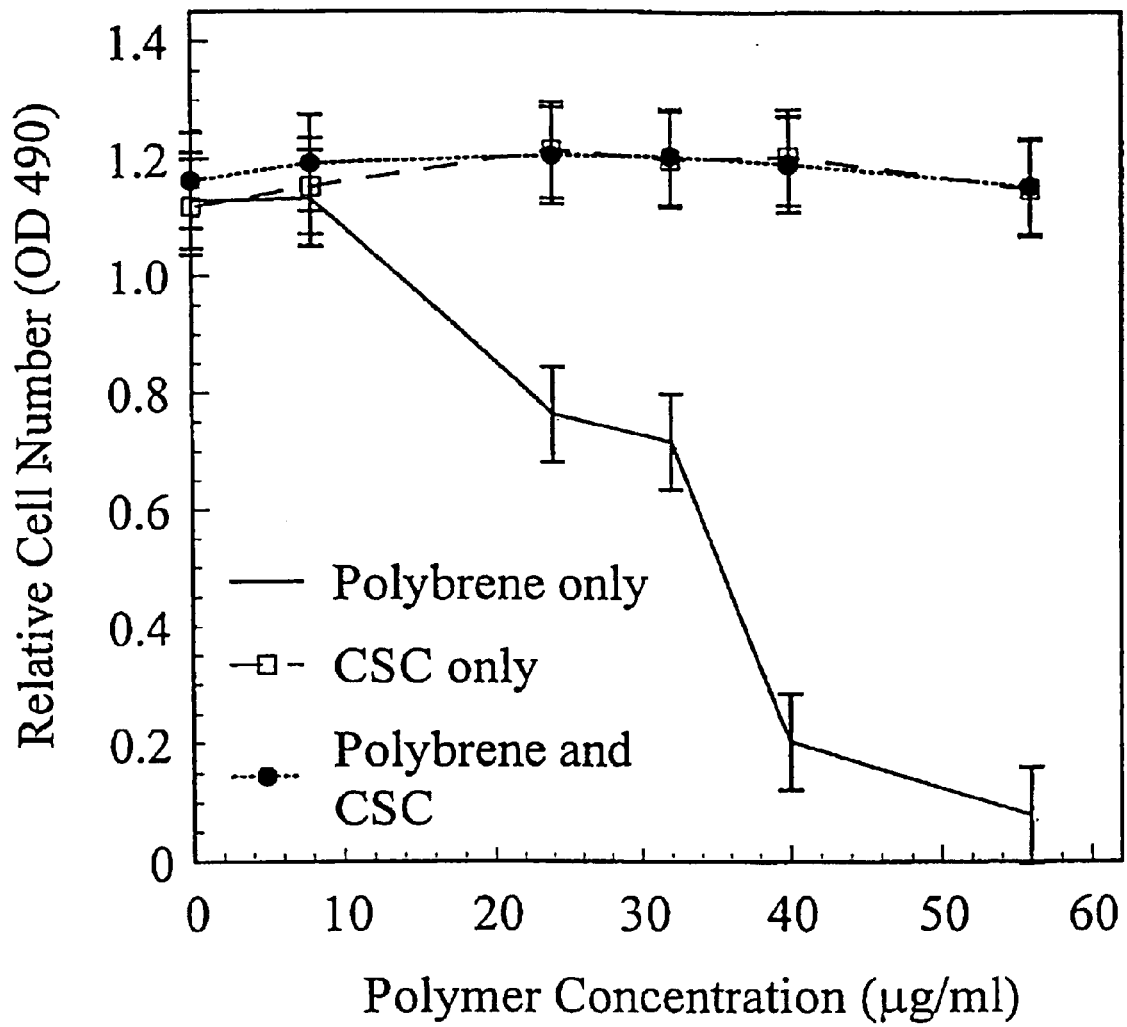
FIG. 4 is a plot of relative cell number (represented by $OD_{490}$ on the y-axis) versus concentration of POLYBRENE® used alone (—), chondroitin sulfate C used alone (-□-), and POLYBRENE® and chondroitin sulfate C used at the same time (-●-).

As indicated in FIG. 4, POLYBRENE® and CSC are not cytotoxic when used together. The data plotted in FIG. 4 were determined by adding various concentrations of POLYBRENE® and CSC to culture medium and then applying it to NIH 3T3 cells plated the previous day at 5000 cells per well in a 96 well plate. The cells were grown for two days, and then were fixed and stained in the Orange G assay for cell number.

Figure 5:
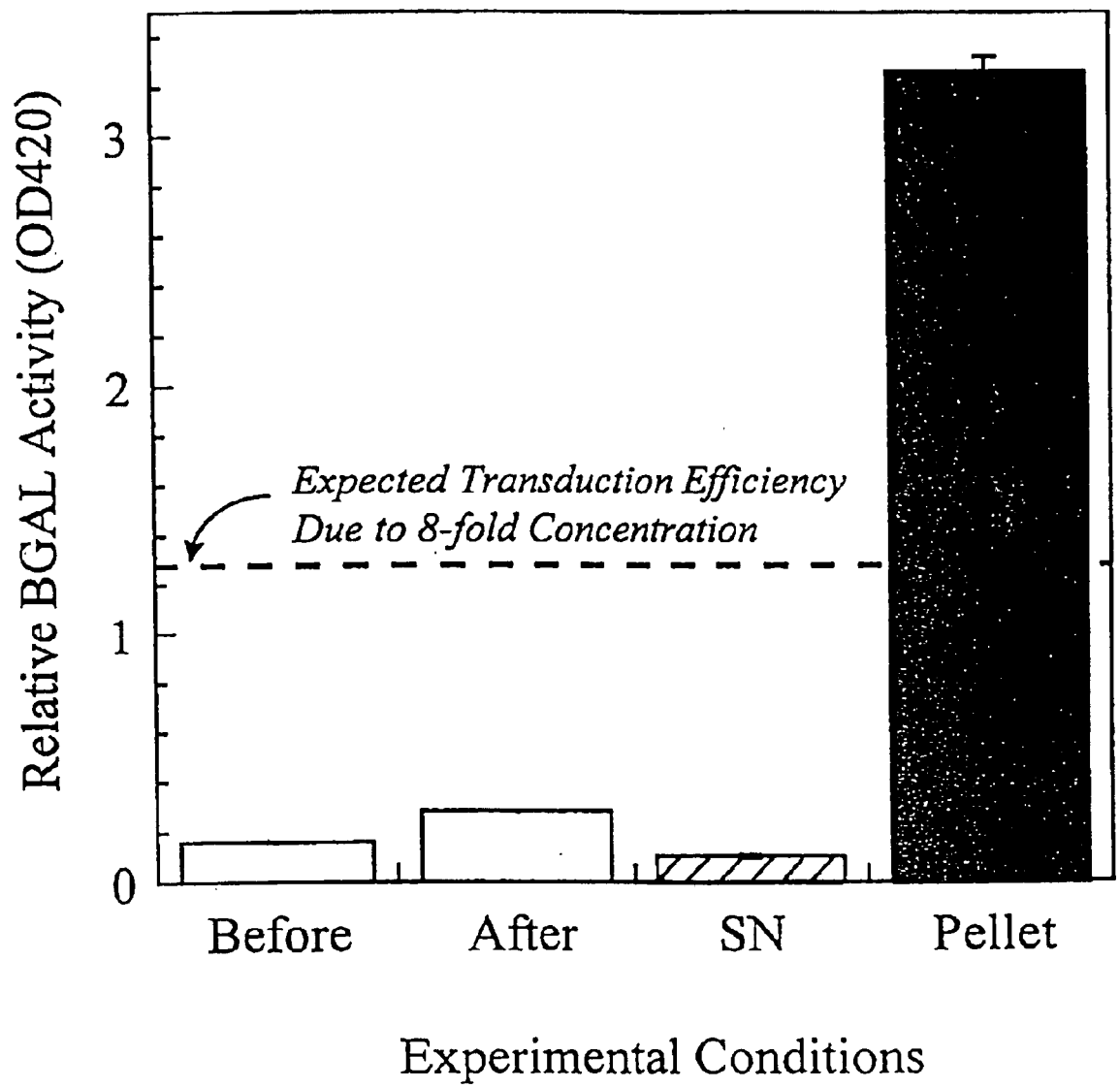
FIG. 5 is a plot of transduction efficiency of viruses taken from the four samples described in FIG. 1, with the exception that the "Pellet" sample was resuspended to only ⅛ of its original volume. The dotted line represents the expected transduction efficiency corresponding to 8-fold concentration. The y-axis represents BGAL activity virus titer (colony-forming units per milliliter (cfu/ml)).

The results show that virus concentrated by pelleting with POLYBRENE® and CSC efficiently transduces cells. A solution resulting from the resuspension of the pellet to ⅛th its original volume with cell culture medium was used to transduce NIH 3T3 cells. The results are represented by the black bar ("Pellet") in FIG. 5. Cells were also transduced with virus stocks before the stocks were centrifuged and before (white bar/"Before"), and after (speckled bar/"After") POLYBRENE® and CSC were added to them. Cells were also transduced by the supernatant (cross hatched bar/"SN") of a virus stock after it had been brought to 80 µg/ml POLYBRENE® and 80 µg/ml CSC and centrifuged. Also shown in FIG. 5 is the expected transduction efficiency of a virus stock that is concentrated 8-fold, given that the concentrated virus does not saturate the cells, no inhibitors were co-concentrated with the viruses, and the viruses are not inactivated by the concentration process (dotted line).

In summary, less than 3 percent of non-viral proteins were concentrated into the pellet (FIG. 3), giving rise to a pellet that contained active viruses (FIGS. 2 and 5) and the polyelectrolyte complexes but almost no spent medium or other substances that might interfere with retrovirus transduction. Importantly, a solution that contains high concentrations of POLYBRENE® and chondroitin sulfate C is not cytotoxic to cells (FIG. 4).

Example 2

Concentration of Lentivirus

The new methods can also be used with lentivirus vectors in a manner similar to that described in Example 1. As described for MMLV in Example 1, stocks of lentiviruses are brought to 80 µg/ml of chondroitin sulfate C, incubated for 10 minutes at 37° C., and then brought to 80 µg/ml of POLYBRENE®, and incubated for an additional 10 minutes at 37° C. The complex of chondroitin sulfate C, POLYBRENE®, and the lentivirus particles is concentrated by low speed centrifugation (e.g., 10,000 rpm for 5 minutes) in a tabletop centrifuge (FIG. 1). The pellet is resuspended in phosphate buffered saline or any other buffer suitable for injection in vivo. The volume of the buffer used to resuspend the viruses is chosen based on the desired final concentration of virus needed to achieve a therapeutic effect. Typically, the pellet is resuspended in a volume that is about 10- to 100-fold less than the initial volume of the virus stock, so that the final concentration of the viruses is 10- to 100-fold greater than the concentration of the viruses in the original virus stock. The virus-polymer solution is then delivered in vivo in such a way as to maximize the transfer of genes to the target cells. For example, to target airway epithelial cells, the virus-polymer solution is injected into the lungs of a patient in the form of an aerosol. The number of genes transferred by this method is substantially higher than with traditional methods because the virus is at a higher concentration and the polymer mixture enhances the efficiency of gene transfer 2- to 3-fold or more.

Example 3

Use of the New Methods in Gene Therapy

The new methods are scalable for large-scale purification and concentration of recombinant retroviruses for use in human gene therapy protocols. Large-scale purification and concentration is important for the ultimate success of many human gene therapy protocols because large numbers of genes generally must be transferred to achieve a desired therapeutic effect. It is estimated that up to 1 liter of retrovirus stocks may have to be used for a typical gene therapy clinical trial to achieve the desired effect. To administer this amount of virus to a patient using traditional methods, the patient is treated several times with smaller volumes of virus. The new methods of the invention can be used not only to enhance the activity and concentration of the virus stocks as described in Examples 1 and 2, but also to reduce the number of times the viruses must be administered to patients to achieve the desired therapeutic effect. Large volumes of retroviruses, produced by standard large-scale cell culture techniques (e.g., microcarrier bioreactors or stirred-tank bioreactors), are brought to appropriate concentrations of cationic and anionic polymers as described in Examples 1 and 2. The virus precipitates are then mechanically separated from the fluid portion of the virus stock on a large scale using sedimenting centrifuges and/or centrifugal classifiers. These machines separate particles from fluid streams in a continuous process and allow the new methods to be used on a large scale to produce retrovirus precipitates useful for human gene therapy protocols.

Example 4

Use of the New Methods to Improve Assay Sensitivity

The new methods are also useful for improving the sensitivity of assays designed to detect pathological viruses in blood or plasma. Blood and plasma samples are often screened for the presence of HIV using PCR to detect the RNA genome of HIV or using an ELISA to detect p24, an HIV capsid protein. The number of HIV particles (viral load) in the blood of AIDS patients is often determined in order to follow the course of the disease. The new methods are used to enhance the sensitivity of these assays. Enhanced sensitivity increases the likelihood of detecting blood or plasma products that are contaminated with HIV and reduces the likelihood that a patient is misdiagnosed as HIV negative due to the poor sensitivity of a diagnostic test for HIV. Blood or plasma samples are brought to 80 µg/ml of CSC and POLYBRENE®, and the resulting precipitates are pelleted by low speed centrifugation as described in Example 1. The pellet is resuspended in $\frac{1}{10}$ to $\frac{1}{100}$ the original volume, effectively concentrating the HIV antigens 10- to 100-fold. The resuspended sample is tested by any of several currently available ELISA kits that test for the presence of HIV antigens. Because the samples are concentrated 10- to 100-fold, and because the polymers do not interfere with ELISAs, the sensitivity of the HIV test is enhanced 10- to 100-fold. Assuming that the polymers do not interfere with PCR reactions, the sensitivity of kits that detect HIV by PCR is also expected to be enhanced 10- to 100-fold.

Example 5

Precipitation and Concentration of a Recombinant Retrovirus Encoding Keratinocyte Growth Factor (KGF)

The new methods were used to precipitate and concentrate a recombinant retrovirus encoding KGF to improve gene transfer and increase the level of KGF secreted by transduced cells.

A stock of amphotropic KGF retrovirus was harvested from a packaging cell line and filtered through a 0.4 micron filter. The stock was brought to 80 µg/ml CSC and 80 µg/ml POLYBRENE®, and the resulting complex was pelleted by centrifugation and resuspended in cell culture medium to one-tenth the original volume. This 10× concentrated KGF virus suspension was used to transduce human diploid fibroblasts overnight. Afterwards, the cells were washed with culture medium, and then allowed to grow to confluence.

Figure 6:
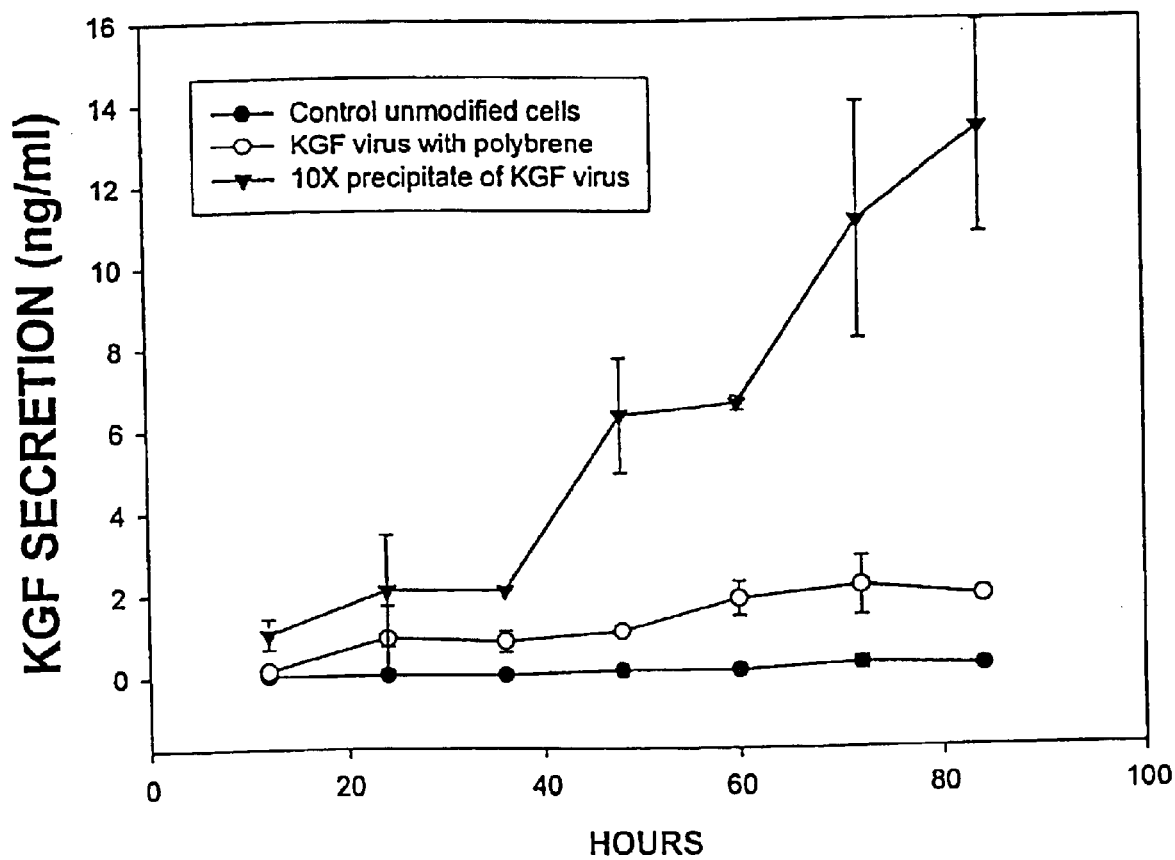
FIG. 6 is a plot of secreted KGF accumulated in the culture medium of control unmodified fibroblasts (Control unmodified cells, -●-), fibroblasts that have been modified with a standard stock of unconcentrated keratinocyte growth factor (KGF) retrovirus to which POLYBRENE® alone (8 µg/ml) has been added (KGF virus with polybrene, -○-), and fibroblasts that have been genetically modified with precipitated KGF virus that was resuspended in one-tenth the original volume (10× precipitate of KGF virus, -▼-), as a function of time, as described in Example 5.

To measure the levels of secreted KGF, the genetically modified human fibroblasts were split into new 10 cm dishes, and grown to confluence. The spent medium was replaced with fresh culture medium (30 ml), and aliquots (1 ml) were removed over time. The levels of KGF secreted by the cells were quantitated using an ELISA specific for KGF. FIG. 6 is a plot of secreted KGF accumulated in the culture medium of control unmodified fibroblasts (Control unmodified cells, -●-), fibroblasts that have been modified with a standard stock of unconcentrated KGF retrovirus to which POLYBRENE® alone (8 µg/ml) has been added (KGF virus with polybrene, -○-), and fibroblasts that have been genetically modified with precipitated KGF virus that was resuspended in one-tenth the original volume (10× precipitate of KGF virus, -▼-), as a function of time. A small amount of KGF is naturally secreted by control diploid human fibroblasts. As illustrated by FIG. 6, this level is enhanced when the cells are transduced with the KGF virus in the conventional manner, and is greatly enhanced when the same virus is precipitated with CSC and POLYBRENE® and resuspended in one-tenth the original volume.

Since KGF is known to stimulate the growth of epidermal keratinocytes of the skin, genetically modified cells (e.g., dermis cells, keratinocytes, epidermal cells) secreting KGF may have uses in promoting wound healing (including, for example, healing of chronic wounds such as diabetic wounds). For example, such cells can be administered to tissue in the vicinity of the wound (e.g., by injection or implantation, optionally together with a pharmaceutically acceptable carrier, optionally containing other pharmaceutical substances), or topically applying the cells to the wound (e.g., in a dressing, film (e.g., a polyurethane film), a hydrocolloid (e.g., hydrophilic colloidal particles bound to polyurethane foam), a hydrogel (e.g., cross-linked polymers containing about at least 60% water), a hydrophilic or hydrophobic foam, or another carrier, e.g., a pharmaceutically acceptable gel, cream, powder, suspension, solution, ointment, salve, lotion, or biocompatible matrix, e.g., a petroleum jelly formulation, optionally containing other pharmaceutical substances such as an antibiotic). The cells can be used to promote healing by, for example, stimulating growth of keratinocytes for use, for example, in wound healing methods (e.g., those described in U.S. Pat. No. 6,197,330). Higher levels of KGF secretion can enhance the therapeutic effectiveness of these cells. Higher levels of KGF secretion can enhance the therapeutic effectiveness of these cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for purifying viruses from a first solution, the method comprising:
   (a) combining the first solution with an anionic polyelectrolyte and a cationic polyelectrolyte, wherein the cationic polyelectrolyte and anionic polyelectrolyte can form complexes with viruses, to form a second solution;
   (b) allowing complexes of the viruses, anionic polyelectrolyte, and cationic polyelectrolyte to form in the second solution, and
   (c) centrifuging the second solution to obtain a supernatant and a pellet, wherein the pellet comprises the viruses.

2. The method of claim 1, wherein the anionic polyelectrolyte is selected from the group consisting of glycosaminoglycans and polysaccharides.

3. The method of claim 2, wherein the glycosaminoglycans and polysaccharides are sulfated.

4. The method of claim 1, wherein the anionic polyelectrolyte is selected from the group consisting of chondroitin sulfates, heparin, heparan sulfate, keratan sulfate, carrageenans, fucoidan, poly-L-glutamic acid, poly-L-aspartic acid, poly(glycolic acid), poly(lactic acid), and poly(lactic-co-glycolic acid).

5. The method of claim 4, wherein the anionic polyelectrolyte is chondroitin sulfate C.

6. The method of claim 1, wherein the cationic polyelectrolyte is a cationic polymer that complexes with the anionic polyelectrolyte.

7. The method of claim 1, wherein the cationic polyelectrolyte is selected from the group consisting of(diethylamino)ethyl dextran, histones, protamine, poly-L-arginine, poly-L-histidine, and poly-L-lysine.

8. The method of claim 1, wherein the cationic polyelectrolyte is hexadimethrine bromide.

9. The method of claim 1, wherein the first solution further comprises proteoglycans.

10. The method of claim 1, further comprising separating the pellet from the supernatant, and then resuspending the pellet in a resuspension buffer.

11. The method of claim 10, wherein the volume of the resuspension buffer is no greater than one-tenth the volume of the solution, thereby resulting in at least a ten-fold concentration of the virus.

12. The method of claim 10, wherein the volume of the resuspension buffer is no greater than one-hundredth the volume of the solution, thereby resulting in at least a one-hundred-fold concentration of the virus.

13. The method of claim 10, wherein the resuspension buffer comprises phosphate-buffered saline.

14. The method of claim 10, wherein the resuspension buffer comprises cell culture medium.

15. The method of claim 10, wherein the resuspension buffer comprises a pharmaceutically acceptable carrier.

16. The method of claim 1, wherein the virus is a retrovirus.

17. The method of claim 1, wherein the virus is an enveloped virus.

18. The method of claim 1, wherein the virus is selected from the group consisting of human immunodeficiency virus, lentiviruses, Moloney murine leukemia virus, herpes simplex virus, Epstein-Barr virus, human cytomegalovirus, influenza viruses, poxviruses, and alphaviruses.

19. The method of claim 1, wherein the anionic polyelectrolyte is added before the cationic polyelectrolyte.

20. The method of claim 1, wherein the anionic polyelectrolyte and the cationic polyelectrolyte are added simultaneously.

21. The method of claim 1, wherein the anionic polyelectrolyte comprises chondroitin sulfate C and the cationic polyelectrolyte comprises hexadimethrine bromide.

22. The method of claim 1, wherein the anionic polyelectrolyte comprises iota carrageenan and the cationic polyelectrolyte comprises DEAE dextran.

23. The method of claim 1, wherein the anionic polyclectrolyte comprises poly-L-glutamate and the cationic polyelectrolyte comprises poly-L-lysine.

24. The method of claim 1, wherein the anionic polyelectrolyte comprises heparan sulfate and the cationic polyelectrolyte comprises protamine.

25. The method of claim 1, further comprising dissociating the virus from the polyelectrolytes.

26. The method of claim 1, wherein the cationic polyelectrolyte is added before the anionic polyelectrolyte.

27. The method of claim 1, further comprising separating the pellet from the supernatant.

* * * * *